Feb. 22, 1949. G. C. SPARRE Plant Pat. 827
CHRYSANTHEMUM PLANT
Filed June 19, 1947
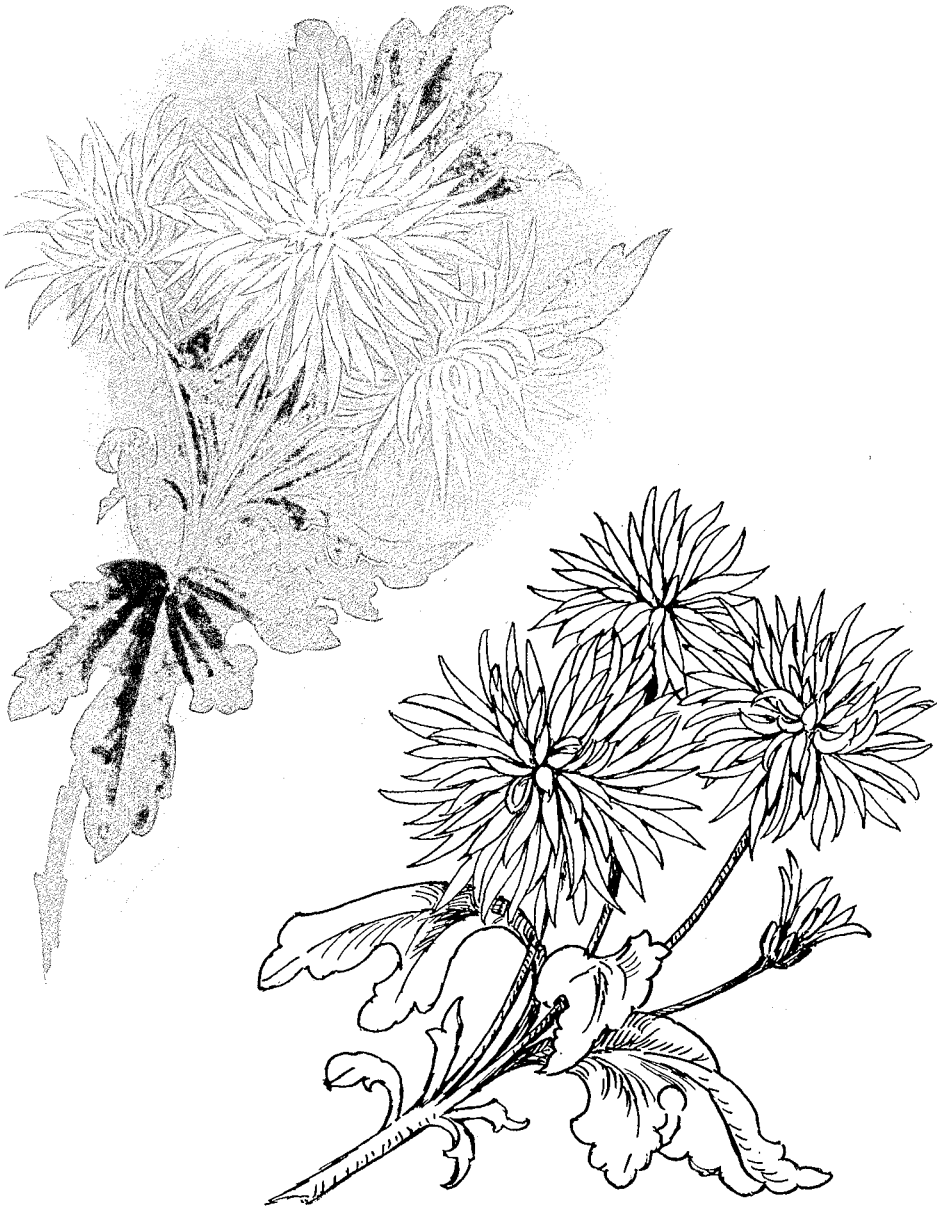
WITNESS
Addison F. Avery
INVENTOR
Gustav C. Sparre,
by: John Harrod Kennedy
his ATTY Patented Feb. 22, 1949

Plant Pat. 827

UNITED STATES PATENT OFFICE

827

CHRYSANTHEMUM PLANT

Gustav C. Sparre, Clarkson, Ontario, Canada, assignor to John J. Grullemans, Mentor, Ohio Application June 19, 1947, Serial No. 755,683

1 Claim. (Cl. 47—60)

This invention relates to a new and distinct variety of chrysanthemum plant.

The drawing shows in one view, in color, the terminal of one of the main stalks with the terminal inflorescence and leaves and a similar view in black and white indicating the structure in more detail.

The variety was produced by me by crossing a chrysanthemum plant Mrs. Dunington Grubb, as the seed parent, with the chrysanthemum plant Snowbird, as the pollen parent, both the seed parent and pollen parent being crosses made by me between *Chrysanthemum indicum* and the Korean strain. The new variety was first produced by me in my gardens at Clarkson, Ontario, Canada, and there was first asexually reproduced by me by root cuttings. The original plant is still growing and cuttings thereof have been grown at my gardens at Clarkson, Ontario, Canada, and in the fields of The Wayside Gardens Company, of Mentor, Ohio.

The plant has a fibrous mass of shallow roots of medium size, having the usual spread which is about equal to the spread of the exposed portion of the plant. The root resistance to disease, wetness and drought is good as also is its winter resistance, both protected and unprotected. Unprotected, the roots have withstood temperatures as low as 12° to 15° (F.) below zero.

The exposed plant is herbaceous, generally upright, oval, and medium compact. It averages from 18 to 20 inches in height the first year and reaches a height of 36 inches in the second or third year. Its spread is about 18 to 24 inches. It is of vigorous growth and the exposed portion of the plant has a good resistance to low temperatures, both protected and unprotected, and also good resistance to disease, drought and wet seasons. It prefers moderate sun and any exposure other than north. It does well in any good garden loam under the usual growing conditions suitable for chrysanthemum plants. It prefers a well drained soil.

The main stalks are upright, herbaceous and very much branched. They are relatively stiff and brittle but generally adequate to support the foliage and blooms well. Both the new and old growth is generally a dark green or grayish green with areas of rose purple, comparable to Maerz and Paul Plate 21–B–3. The main stalks vary in length from 30 to 36 inches, having a smooth surface texture and grow divergently from the roots. The branches are whorled, of dark green color and of a hirsute texture. The leaves are abundant and of whorled arrangement. The top of the new leaves is generally a dull green, comparable to Maerz and Paul Plate 24–L–6, and the bottom of the new leaves is generally of a light green, comparable to Maerz and Paul Plate 22–I–6. The old leaves are slightly darker but the color is generally uniform. The leaves are of average shape and size and of medium thickness with hirsute upper and lower surfaces. Their persistency on the plant is excellent. The peticles are dull green, smooth and of medium strength.

The plant thrives well throughout substantially the entire United States, preferring a sunny southern exposure which is reasonably moist and fairly cool during the blooming season. It prefers a neutral, moist but well drained rich loam soil. The quality and quantity of the blooms are best when there is at least a half day's sun combined with cool weather and a fairly moist soil. The color is not affected by changes in these conditions. The number of blooms produced is about the same under all growing conditions except that none is produced in deep shade. Heat and shade tend to reduce the size of the blooms but cause no change in color.

The blooming period extends through the month of September, sometimes starting as early as the latter part of August. The plant blooms continuously during the blooming period and the blooming period is lengthened by removal of the old flowers.

The buds are of the usual globular shape and are borne generally upright. When the sepals first divide they are a deep lilac which changes to a deep rosy lilac as the petals begin to unfurl and become a rosy lilac when they are half blown. When full blown, the blooms are a lilac color, ranging from Maerz and Paul Plate 49–A–4 to 49–D–6, with a faint yellow center, comparable to Maerz and Paul Plate 9–E–1.

The blooms average in size from three to four inches in diameter and are borne thirty to fifty on the average plant in heads or open clusters of three or four to a stem. They are very persistent and long lasting on the plant and are long lasting when cut.

The color of the petalage is a rosy lilac and is the same for the center of the flower, the outer petals, the base of the petals and the reverse of the petals. The general tonality from a distance is rosy lilac and there is little or no change in color during the blooming season. The petals are waxy and smooth, both inside and outside and are lanceolate, very narrow and pointed at both ends. They are arranged similar to the petals of a cactus dahlia but are not imbricated. The blooms are fully double and shaggy so that the entire bloom is similar to a cactus dahlia. The blooms are globular and graceful in appearance, being free from petaloids at the center. They have a faint chrysanthemum fragrance.

The stamens are composite. The fruit is usual in appearance, in significant and sparse. The blooms are produced in open clusters which permits a fine showing of their details.

I claim:

The new variety of chrysanthemum plant herein shown and described, characterized in that its flowers are produced in open clusters, are fully double, are shaped like a cactus dahlia and are large yet very graceful in appearance and have an exceptional rose lilac color, and the plant is exceedingly vigorous, of exceptional resistance to disease and of good resistance to drought, and its roots have the ability to withstand severe winters, both protected and unprotected.

GUSTAV C. SPARRE.

No references cited.